United States Patent [19]

Battisti et al.

[11] 4,252,566

[45] Feb. 24, 1981

[54] CUMARINIC PIGMENTS

[75] Inventors: Ruggero Battisti, Novara; Giovanni Bausani, Trecate; Francesco Casagrande; Nicola Mazzaferro, both of Novara, all of Italy

[73] Assignee: Montedison S.p.A., Milan, Italy

[21] Appl. No.: 111,200

[22] Filed: Jan. 11, 1980

[30] Foreign Application Priority Data

Jan. 15, 1979 [IT] Italy ............................... 19278 A/79

[51] Int. Cl.³ .......................................... C07D 311/06
[52] U.S. Cl. ................................. 260/343.44; 106/22; 106/288 Q
[58] Field of Search ........................... 106/22, 288 Q; 260/343.42, 343.44, 343.45

[56] References Cited

PUBLICATIONS

Journal of Heterocyclic Chemistry, 12 (1975) 417.

Primary Examiner—Hosea E. Taylor
Assistant Examiner—Amelia S. Yarbrough
Attorney, Agent, or Firm—Morgan, Finnegan, Pine, Foley & Lee

[57] ABSTRACT

The present invention concerns a new class of pigments derived from cumarin and, more particularly, of bis-iminocumarinic and bis-cumarinic pigments having the following formula I described hereinlater. The present invention also includes novel processes for making the cumarinic pigments of the invention. Also, the invention relates to the use of the novel pigments of the invention for the preparation of paints, storing enamels, inks and pastes for the printing of fabrics. Also, included in this invention is the dyeing of plastic materials with the novel cumarinic pigments.

5 Claims, No Drawings

CUMARINIC PIGMENTS

BACKGROUND OF INVENTION

The pigments of this invention are believed to be novel and distinct and no prior art is known which is relevant thereto.

OBJECTS OF THE INVENTION

An object of this invention is that of providing a new class of pigments that shall display excellent characteristics for the uses herein above specified. It is a further object of this invention to provide a process for the production of said new pigments. A further object is to provide plastic materials containing such pigments. A still further object is to use said pigments in the preparation of paints, stoving enamels, inks and pastes for fabrics.

This and other objects still, which will appear even more clearly to the skilled of the Art from the following description.

GENERAL DESCRIPTION OF THE INVENTION

As indicated earlier, the present invention relates to novel cumarinic pigments having the formula I:

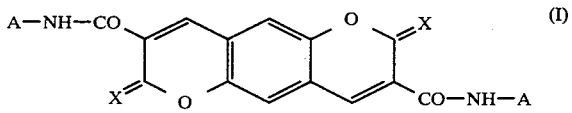

wherein:
A represents a phenyl, a naphthyl, an anthraquinonyl, an heterocyclic group such as benzotriazol, pyrazol, pyridine, isoindazol or benzimidazol, and any of the foregoing groups substituted with groups selected from the group consisting of hydroxyl, halogens, alkyl and/or alcoxyl groups having from 1 to 4 carbon atoms, the carboxylic, the carbamoylic, the benzamidic, the acylaminic, the benzoylaminic, the dialkylaminic groups having in the alkyl portion from 1 to 4 carbon atom, the ureidic, the thioureidic, the trifluoromethylic, the sulphomethylic groups, the nitro-, the cyano-, the arylazo- group also in their turn substituted in the arylic group with a group selected from the group consisting of alkyls, alcoxyls having up to 4 carbon atoms, the halogens and the cyano-group, and
X may be NH or O.

In the following structure (I) with X=NH will be indicated as (Ia) while that with X=O will be indicated as (Ib).

The present invention concerns, moreover, the preparation of the pigments having formula (I), as well as their use.

The pigments of formula (I) are insoluble in water and in most of the organic solvents. These pigments confer a coloring of a yellow to red tinge, with a good dyeing power, an excellent fastness to light and resistance to migration and to overcoating.

The pigments of this invention find their use in the pigmentation of plastic materials such as for instance polyvinyl chlorides, polystyrenes, polyolefines, and in the preparation of paints, stoving enamels, inks and pastes for the printing of fabrics.

In preparing the cumarinic pigments of this invention, a compound of formula (II):

$$A-NH-CO-CH_2-Y \quad (II)$$

wherein A has the meaning indicated previously hereinabove, and where Y may be CN, or $COOR_1$, wherein $R_1$ is an alkyl group having up to 4 carbon atoms, is made to condense with 2,5-dihydroxyterephthaldehyde (III):

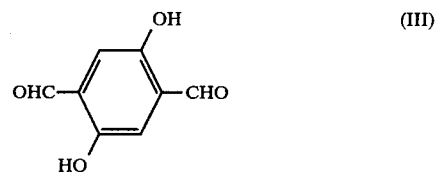

in an organic solvent in the presence of absence of a basic organic catalyst, at a temperature comprised between 50° C. and about 200° C., but preferably at the boiling temperature of the solvent.

The pigments of formula Ia (with X=NH) are thus obtained, more particularly, by condensing products with structure (IV), that is, from compound (II) with Y=CN, with dialdehyde (III) according to reaction (1):

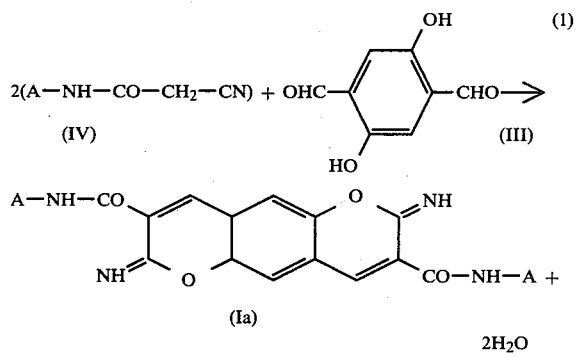

wherein A has the meaning previously indicated.

In practice, by operating according to substantially conventional or known methods, intermediate (IV) is dissolved in an organic solvent and the solution is then treated with aldehyde (III) in the presence or absence of an organic basic catalyst, reflux heating the solution for about 15-60 minutes. A precipitate is thereby formed which is then filtered, washed and dried. Compounds (Ia) thus obtained, are in general very pure.

By treating compounds (Ia) with a mineral acid (hydrochloric acid, sulphuric acid, etc.) there are obtained compounds (Ib) with X=O.

Compounds (Ib) may also be obtained, according to an effective alternative, by condensation of products of formula (V), that is, from compound (II) with Y=$COOR_1$, with the dialdehyde (III) according to reaction (2):

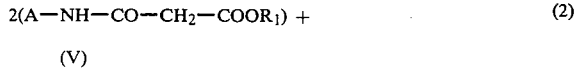

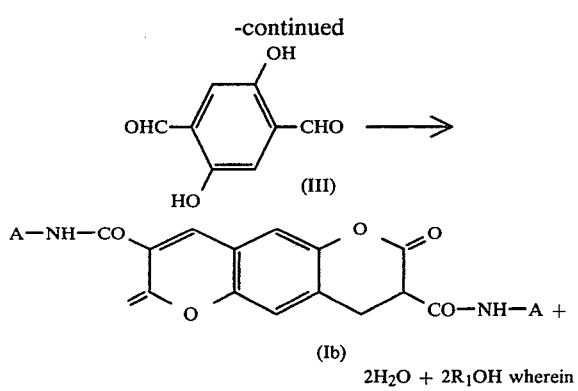

A and $R_1$ have the meaning already indicated.

In practice, intermediate (V) is dissolved in an organic solvent and the obtained solution is then treated with dialdehyde (III) in the presence or absence of a basic organic catalyst, by reflux heating the mixture for about 15 to about 60 minutes. Thereby forms a precipitate which is then filtered, washed and dried. As organic solvents for the reactions (1) and (2) there may be used chlorobenzene, dichlorobenzene, dimethylformamide, dimethylacetamide, etc.

Amongst the basic organic catalysts usable whenever wished for reactions (1) and (2), there may be cited: pyridine, piperidine, N-alkyl-piperidines, having up to 4 carbon atoms in the alkyl portion, pyrrolidone, morpholine, triethylamine, in molar quantities comprised between 0.01 and 0.2 mols per mol of aldehyde (III).

The intermediate of formula (IV), which participates in reaction (1), is in its turn obtained by condensation between an amine derivative of formula (VI) and the compound of formula (VII) according to reaction (3):

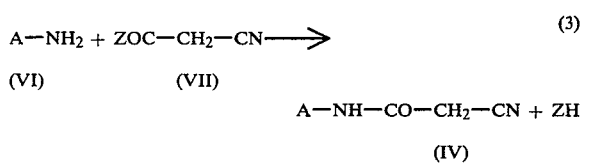

wherein A has the meaning already specified, while Z=OH, $OR_2$, wherein $R_2$ represents a lower alkyl having up to 4 carbon atoms.

Reaction (3) is conducted according to known techniques such as for instance by condensation of the amino-derivative (VI) with the cyan-acetic ester (VII), in which Z=$OR_2$, or with cyan-acetic acid (VII), wherein Z=OH, in the presence of $PCl_5$.

Intermediate (V) which participates in reaction (2), is obtained in its turn by condensation in the same solvents of the amino-derivative (VI) with the malonic diester of formula (VIII), according to reaction (4):

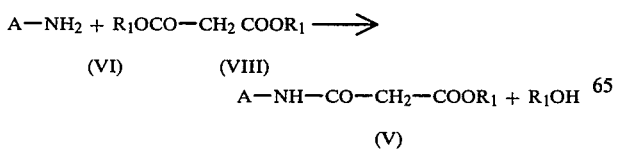

where A and $R_1$ have the meaning already previously specified. Amongst the amino-derivatives of formula (VI) there may be cited: amino-azo-toluene, amino-azo-benzene, 4(2-benzoylamino-5-methoxy-4-aminophenylazo)-3-methyl-chlorobenzene, 3-(2,5-dimethoxy-4-amino-phenylazo)-4-cyano-chlorobenzene, 3-(2,5-dimethoxy-4-amino-phenylazo)-1-phenyl-pyrazol,3-(2-acetyl-amino-5-methoxy-4-amino-phenylazo)-1-(3,4-dichlorophenyl)-pyrazol, 4-(2-acetylamino-5-methoxy-4-amino-phenylazo)-3-cyano-nitrobenzene, 2,methoxy-aniline, 2,5-dimethoxy-aniline, 4-chloro-aniline, 2,4-dichloro-aniline, 2,4,6,-trichloroaniline, 2-methoxy-5-acetylamino-aniline, piperidine, 2-methoxy-5-carbamoyl-aniline, N,N-dimethyl-p-phenyldiamine, 2-aminobenzothiazol, 3-amino-1-phenyl-pyrazol, 1-naphthylamine, 1-amino-antraquinone, 1-amino-4-hydroxyantraquinone, 2,5-dimethoxy-4-chloro-aniline etc.

The dihydroxyterephthaldehyde (III) may be prepared according to known techniques, for instance like those described in Journal of the Chemical Society (1965) 438 and in Journal of Heterocyclic Chemistry (1975) 417.

The pigments obtained according to this invention in general appear already directly suited for the use, without any further treatments. The applicational techniques are those corresponding to the conventional techniques well known to those versed in the art.

SPECIFIC DESCRIPTION OF THE INVENTION

The examples given in the following have only an illustrative purpose and shall not be intended in any restrictive way of the scope of the invention.

EXAMPLE 1

22.5 g of aminoazotoluene were dissolved in 100 ml of dimethylformamyde, and to this solution were then admixed 71.5 g of ethyl cyanoacetate. This mixture was then reflux-heated for about three hours, at the same time drawing off 50 ml of heads. After cooling down and acidification with hydrochloric acid, the solution was then diluted with water, filtered, washed to neutrality and finally the precipitated cyanacetarylide was dried: intermediate (IV) with

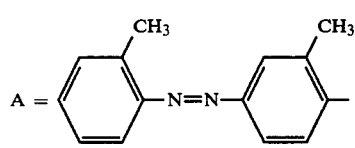

14.6 g of the cyanacetarylide thus obtained were dissolved in 117 ml of dimethylformamyde and to this solution were then added 4.15 g of 2,5-dihydroxyterephthaldehyde and this mixture was then reflux-heated for thirty minutes.

The solution was then cooled down and the precipitate was filtered by washing with ethanol.

The pigment obtained after drying was a yellow tinged powder of the formula:

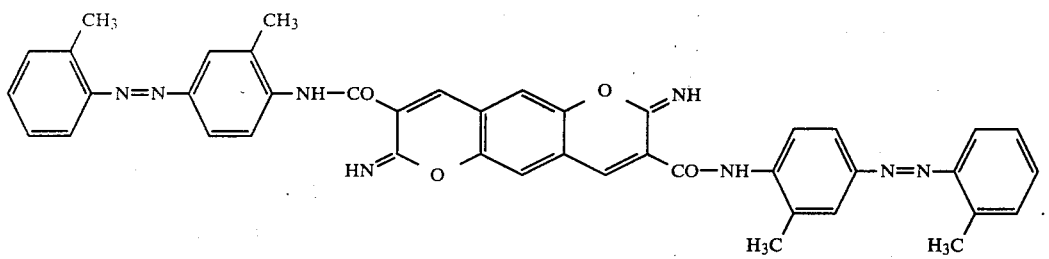

The percentual analysises and the IR spectrum agree with the suggested structure.

EXAMPLE 2: (applicational)

5 g of the pigment obtained according to example 1 were dispersed in a ball mill in 95 g of an enamel medium consisting of 22% of alkydic resin, 19% of melaminic resin and 59% of xylene.

The enamel thus obtained, applied and dried for 30 minutes at 125° C., displayed a deep and pure yellow-orange tinge, of high fastness to light, to overpainting and to heat.

EXAMPLE 3 (applicational)

0.3 g of the pigment obtained according to example 1 were dispersed in 70 g of polyvinyl chloride Sycron 548 (a trade mark by Montedison) and 30 g of dioctylphthalate for 4 minutes in a bicylindrical mixer at 150° C., thereby obtaining 0.3 mm thick sheets coloured in a deep yellow-orange tinge of excellent fastness to light and migration.

EXAMPLE 4

11.25 g of aminoazotoluene were dissolved in 50 ml of dimethylformamyde, and in this solution, reflux-heated, there were dripped in about two hours 11.2 g of diethylmalonate dissolved in 40 ml of dimethylformamyde, at the same time drawing off 20 ml of heads.

Once the addition had been completed, heating was carried on for another 2 hours while drawing off was continued, and there were thereby gathered about further 20 ml of heads.

Thereupon, the solvent was removed under vacuum and the residue was diluted with little ethanol and, after filtering and successive drying, there was obtained malonarylide-ethylester: intermediate (V) with

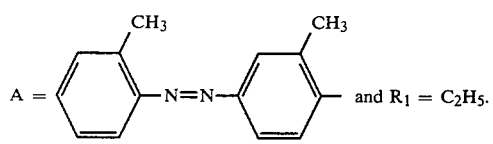

To 8.48 g of the malonarylide-ethylseter thus obtained, dissolved in 60 ml of dimethylformamide, were admixed 2.075 g of 2,5-dihydroxyterephthaldehyde, and this mixture was then refluxheated for thirty minutes. The mixture was then cooled down and the precipitate was filtered off by washing with methanol.

The pigment thus obtained after drying turned out to be a red-orange coloured powder of formula:

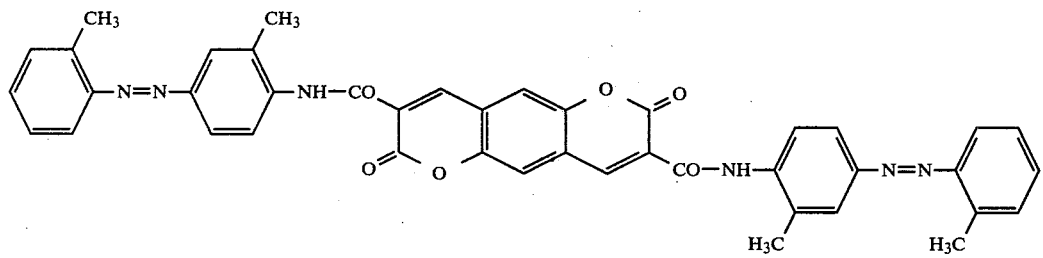

The percentual analysises and the IR spectrum agreed with the suggested structure.

The pigment, applied according to example 2, yielded a pure deeply orange tinged enamel displaying a high fastness to light, to overpainting and to heat. Used in PVC, according to example 3, this pigment yielded deeply orange tinged sheets having an excellent fastness to light and migration.

EXAMPLE 5

7.14 g of the pigment obtained according to example 1 were dispersed in 100 ml of dimethylformamide and then treated with 100 ml of HCl at 36° Be, whereafter they were reflux-heated for 15 hours. The mixture was then cooled down, filtered and washed to neutrality with water. After drying, the pigment obtained was identical with that obtained according to example 4.

EXAMPLE 6

25 g di 1-(m-chlorophenyl)-3-aminopyrazol were dissolved in 250 ml of dimethylformamide and to this solution were then added 75 g of cyanoacetate of ethyl. The solution was then reflux-heated for about five hours at the same time drawing off about 125 ml of heads.

After cooling and acidification with hydrochloric acid, the solution was diluted with water, filtered, washed to neutrality and the precipitated cyanacetarylide was dried: intermediate (IV) with:

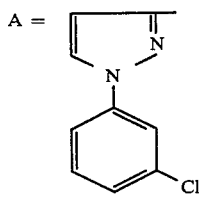

9 g of the cyanacetarylide thus obtained were dissolved in 50 ml of o-dichlorobenzene and to this solution were then added 3.32 g of 2,5-dihydroxy-terephthaldehyde and 0.05 g of piperidine, after which the solution was reflux-heated for fifteen minutes. Thereafter the solution was cooled down and the precipitate was filtered off by washing with methanol. The pigment obtained after drying was a yellow tinged powder of the formula:

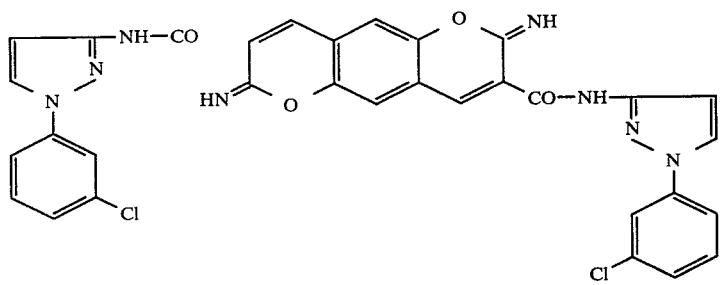

The percentual analysises and the IR spectrum agreed with the suggested structure.

The pigment, applied according to example 2, yielded an enamel of a deep, pure yellow tinge, of a high fastness to light, to overpainting and to heat. Used in PVC, according to example 3, it gave sheets coloured in a deep yellow of excellent fastness to light and migration.

EXAMPLE 7

5 g of the pigment obtained according to example 6, were dissolved in 25 ml of $H_2SO_4$ at 65° Be and then heated for six hours at 60° C. This solution was then cooled down, poured into water and ice, and filtered by washing to neutrality with water. After drying, the pigment thus obtained was an orange colored powder of the formula:

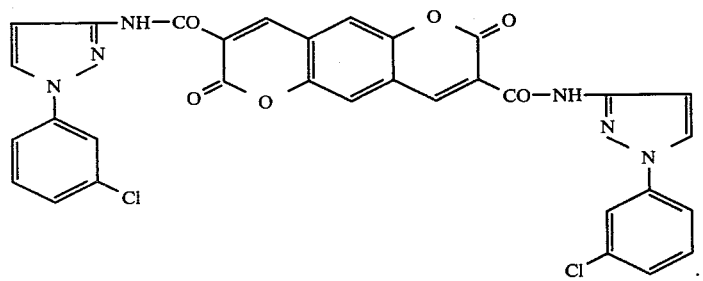

The percentual analysises and the IR agreed with the suggested structure. The pigment, applied according to example 2, yielded an enamel of a deep pure orange tinge, of a high fastness to light, to overpainting and to heat. Applied to PVC, according to example 3, it gave sheets coloured in a deep orange of excellent fastness to light, and to migration.

In a similar way to that of the above described examples there were prepared pigments having the formula;

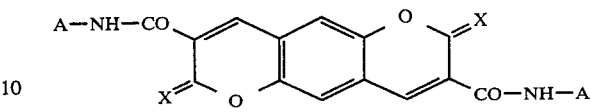

wherein the meanings of A and X and the applications in PVC appear from the following Table.

TABLE

| EXAMPLE | A | X | SHADE on PVC |
|---|---|---|---|
| 8 |  | NH | YELLOW |
| 9 | 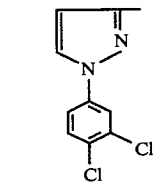 | O | ORANGE |
| 10 | 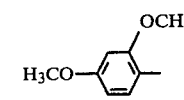 | NH | YELLOW |
| 11 | " | O | ORANGE |
| 12 |  | NH | ORANGE |
| 13 | " | O | RED |

TABLE-continued

| EXAMPLE | A | X | SHADE on PVC |
|---|---|---|---|
| 14 | 4-Cl, 2-CH₃-phenyl-N=N-(2,5-di-OCH₃,4-CH₃)phenyl | O | ORANGE |
| 15 | 4-(H₅C₂OOC)-phenyl | NH | YELLOW |
| 16 | " | O | YELLOW |
| 17 | 4-Cl, 2-CH₃-phenyl-N=N-(4-OCH₃, 5-CH₃, 2-NHCOC₆H₅)phenyl | O | ORANGE |
| 18 | 4-Cl, 2-CH₃, 5-OCH₃, 4-H₃CO-phenyl | NH | YELLOW |
| 19 | " | O | ORANGE |
| 20 | 3-O₂N-phenyl | NH | YELLOW |
| 21 | 4-HO-phenyl | NH | ORANGE |
| 22 | 1-(3,4-diCl-phenyl)pyrazol-3-yl-N=N-(4-OCH₃, 5-CH₃, 2-NHCOCH₃)phenyl | O | ORANGE |
| 23 | 2-OH, 4-CH₃-phenyl | NH | ORANGE |
| 24 | " | O | RED |
| 25 | 4-Cl, 3-HOOC-phenyl | NH | YELLOW |
| 26 | 4-OCH₃-phenyl-NH-CO-phenyl | NH | YELLOW |
| 27 | 2-OCH₃-phenyl | NH | YELLOW |
| 28 | " | O | ORANGE |
| 29 | 4-OCH₃, 3-CH₃, (NHCOCH₃)-phenyl | NH | YELLOW |
| 30 | 1-(3-Cl-phenyl)pyrazol-3-yl-N=N-(4-OCH₃, 5-CH₃, 2-H₃CO)phenyl | O | ORANGE |
| 31 | 2,4,6-triCl, 3-CH₃-phenyl | O | YELLOW |
| 32 | 4-Cl, 2-CN-phenyl | O | YELLOW |

We claim:
1. Cumarinic pigments of formula (I):

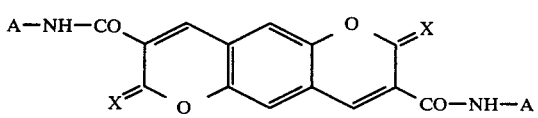

wherein:
A represents a group selected from the group consisting of phenyl, naphthyl, anthraquinonyl, an heterocyclic group and any of the foregoing groups substituted with groups selected from the group consisting of hydroxyl, halogens, the alkyl and/or alcoxyl groups having 1 to 4 carbon atoms, the carboxyl, the carbamoyl, the benzamidic, the acylaminic, the benzoylaminic, the dialkylaminic groups having from 1 to 4 carbon atoms in the alkyl, the cyano-, the ureidic, the thioureidic, the trifluoromethylic, the sulphomethylic, the nitro, the arylazo groups also in their turn substituted in the aryl group with a group selected from the group consisting of alkylic and alcoxylic groups having up to 4 carbon atoms, the halogen and the cyano-groups;
X represents NH or O.
2. Cumarinic pigments according to claim 1 wherein the heterocyclic group is selected from the group consisting of benzotriazol, pyrazol, pyridine, isoindazol and benzoimidazol groups.

3. Process for the preparation of the pigments having the formula indicated in claim 1, characterized in that said pigments are obtained by condensation of a compound of the formula (II):

$$A-NH-CO-CH_2-Y \quad (II)$$

wherein A has the meaning given in claim 1, and Y is selected from the group consisting of CN and $COOR_1$, wherein $R_1$ represents an alkyl group having up to 4 carbon atoms, with 2,5-dihydroxyterephthaldehyde of formula (III):

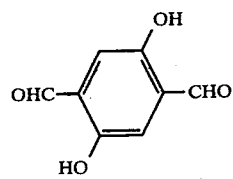

in an organic solvent, possibly in the presence of an organic basic catalyst, at temperatures comprised between 50° and about 200° C.

4. Process according to claim 2, characterized in that the organic solvent is selected from the group consisting of chlorobenzene, dichlorobenzene, dimethylformamide and dimethylacetamide.

5. Process according to claims, 1, 2, 3 or 4 characterized in that the organic basic catalyst is selected from the group consisting of pyridine, piperidine, the N-alkylpiperidines having up to 4 carbon atoms in the alkyl, pyrrolidone, morpholine and triethylamine, in molar quantities comprised between 0.01 and 0.2 mols per mol of aldehyde (III).

* * * * *